United States Patent
Bogert

(10) Patent No.: US 8,673,099 B2
(45) Date of Patent: Mar. 18, 2014

(54) COMPRESSED INNER COVERING HINGED SEGMENTED STENT-GRAFT

(75) Inventor: David L. Bogert, Prescott, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 1166 days.

(21) Appl. No.: 12/441,027

(22) PCT Filed: Aug. 30, 2007

(86) PCT No.: PCT/US2007/077269
§ 371 (c)(1),
(2), (4) Date: Jul. 20, 2009

(87) PCT Pub. No.: WO2008/033678
PCT Pub. Date: Mar. 20, 2008

(65) Prior Publication Data
US 2010/0063574 A1    Mar. 11, 2010

Related U.S. Application Data

(60) Provisional application No. 60/844,556, filed on Sep. 14, 2006.

(51) Int. Cl.
*B32B 37/00*    (2006.01)
(52) U.S. Cl.
USPC ........... 156/165; 156/169; 156/171; 156/173; 156/187; 156/229; 623/1.13; 623/1.15; 623/1.16
(58) Field of Classification Search
USPC ......... 156/165, 169, 171, 173, 187, 229, 293, 156/294, 303; 623/1.13, 1.15, 1.16
See application file for complete search history.

(56) References Cited

U.S. PATENT DOCUMENTS

| | | | |
|---|---|---|---|
| 4,955,899 A | | 9/1990 | Della Corna et al. |
| 5,788,626 A | * | 8/1998 | Thompson ................... 623/1.15 |
| 6,159,531 A | * | 12/2000 | Dang et al. .................... 427/2.24 |
| 6,319,279 B1 | * | 11/2001 | Shannon et al. ............. 623/1.44 |
| 6,361,556 B1 | | 3/2002 | Chuter |
| 6,881,221 B2 | * | 4/2005 | Golds .......................... 623/1.13 |
| 2001/0032009 A1 | | 10/2001 | Layne et al. |
| 2002/0004677 A1 | | 1/2002 | Jayaraman |
| 2003/0180488 A1 | * | 9/2003 | Lim et al. ..................... 428/35.2 |
| 2004/0098095 A1 | * | 5/2004 | Burnside et al. ............. 623/1.13 |

FOREIGN PATENT DOCUMENTS

| | | | |
|---|---|---|---|
| WO | WO 9721403 A1 | * | 6/1997 |
| WO | 0101887 A9 | | 4/2001 |
| WO | 2008027188 A3 | | 4/2008 |

OTHER PUBLICATIONS

PCT/US2007/077269 filed Aug. 30, 2007 International Preliminary Report on Patentability and Written Opinion dated Mar. 17, 2009 and Sep. 4, 2008.
PCT/US2007/077269 filed Aug. 30, 2007 International Search Report dated Sep. 4, 2008.
EP 07841634.4 European Search Report dated Oct. 1, 2012.

* cited by examiner

*Primary Examiner* — Christopher Schatz
(74) *Attorney, Agent, or Firm* — Rutan & Tucker, LLP

(57) ABSTRACT

An implantable prosthesis including a longitudinally compressed generally tubular substrate defining a longitudinal axis, a plurality of expandable segments disposed over the substrate and spaced apart along the longitudinal axis, and a graft member positioned over the segments. The graft member may include a lattice structure. Adjacent expandable segments may be connected by one or more filaments.

17 Claims, 4 Drawing Sheets

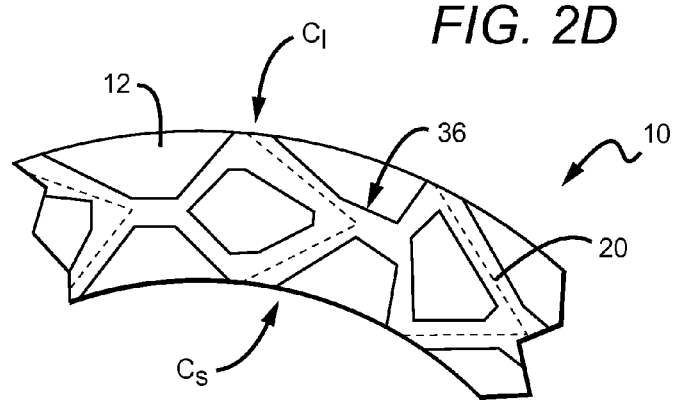
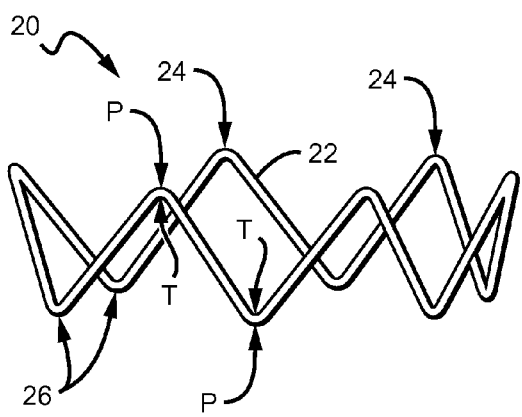
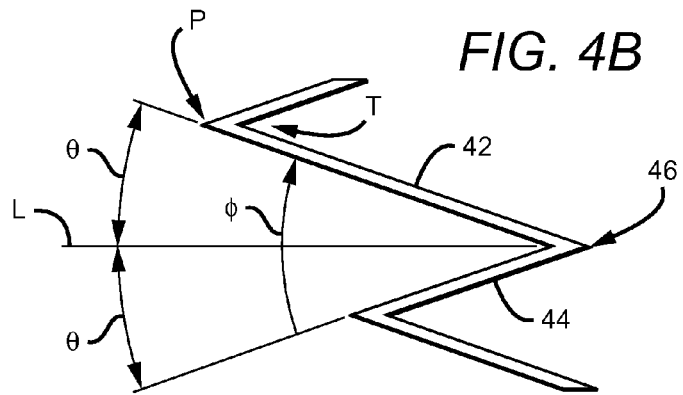
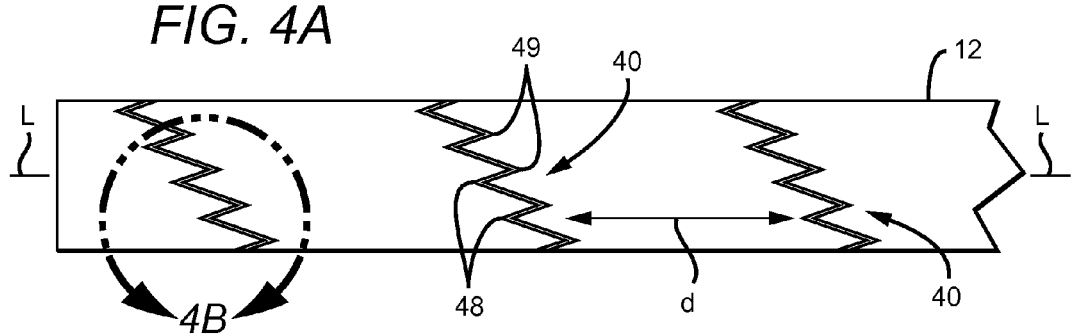

COMPRESSED INNER COVERING HINGED SEGMENTED STENT-GRAFT

PRIORITY

This application is a U.S. national stage application under 35 USC §371 of International Application No. PCT/US2007/077269, filed Aug. 30, 2007, which claims the benefit of priority to U.S. Provisional Patent Application No. 60/844,556, filed Sep. 14, 2006, each of which is incorporated by reference into this application as if fully set forth herein.

BACKGROUND

Intraluminal prostheses used to maintain, open, or dilate blood vessels are commonly known as stents. Stent constructions generally include lattice type cylindrical frames that define a plurality of openings. Common frameworks for stents include, for example, individual rings linked along the length of the stent by a linking member, a continuous helically wrapped member (that may include one or more linking members), a braid or a mesh formed into a tubular structure, and a series of interconnected struts. Stents may be formed by arranging one or more members in a pattern along a longitudinal axis to define essentially a cylinder and connecting the one or more members or otherwise affixing them in position (e.g., interconnecting with a filament). Stents may also be formed by cutting openings into a tube of material (e.g., shape memory).

Stents may have self-expanding and/or balloon expandable properties. Self-expanding stents are delivered to a blood vessel in a collapsed condition and expand in vivo following the removal of a constraining force and/or in the presence of an elevated temperature (due to material properties thereof), whereas balloon expandable stents are generally crimped onto a balloon catheter for delivery and require the outwardly directed force of a balloon for expansion. Stents can be made of various metals and polymers and can include a combination of self-expanding and balloon expandable properties.

Synthetic vascular grafts are routinely used to restore the blood flow in patients suffering from vascular diseases. For example, prosthetic grafts made from expanded polytetrafluoroethylene (ePTFE) are commonly used and have shown favorable patency rates, meaning that depending on a given time period, the graft maintains an open lumen for the flow of blood therethrough. Grafts formed of ePTFE include a microstructure characterized by spaced apart nodes connected by fibrils, the distance between the nodes defined as internodal distance (IND), and are generally extruded either as a tube or as a sheet or film that is fashioned into a tube. Grafts can also be created from fibers woven or knitted into a generally tubular shape.

It is known in the art to use stents in combination with vascular grafts to form stent-grafts. Because stent-grafts are often intraluminally deployed in vessels of varying sizes and tortuosity, flexibility can be an important consideration. Flexibility can be imparted to a stent-graft in a variety of ways, including, for example, connection of the stent to the one or more graft layers, configuration of the stent and/or graft layer(s), spacing of the stent struts, rings, or members along the length of the graft(s), etc. For example, U.S. Pat. No. 6,398,803 and U.S. Pat. No. 6,770,087 to Layne et al., which are incorporated by reference in their entirety into this application, describe a graft layer with openings to enhance flexibility. Another important consideration in the design of a stent-graft is the ability of the stent to withstand stress and fatigue, caused, for example, by plastic deformations occurring at strut junctions when the stent is subjected to circumferential forces. Stent strength can be enhanced through material choice, stent configuration, arrangement and configuration of graft layers, connecting members between stent members, etc. Another consideration in the design of certain stent-grafts is properties to resist kinking of the stent-graft. For example, when a stent-graft is positioned in a bend in a blood vessel or bypass graft, depending on the acuteness of the angle of the bend, the stent-graft can potentially kink and thereby become unsuitable for passage of blood therethrough.

The following references relate to stents and stent-grafts: U.S. Pat. No. 5,104,404 to Wolff; U.S. Pat. No. 5,507,771 to Gianturco; U.S. Pat. No. 6,605,110 to Harrison; U.S. Pat. No. 6,673,103 to Golds et al.; U.S. Pat. No. 6,875,228 to Pinchasik et al.; and U.S. Pat. No. 6,881,221 to Golds, each of which is incorporated by reference in its entirety into this application.

Applicant has recognized that it would be desirable to provide a stent-graft that is flexible, kink-resistant and able to maintain strength under high stress/fatigue environments, embodiments of which are described herein along with methods of making same.

BRIEF SUMMARY

Accordingly, in one embodiment an implantable prosthesis includes a longitudinally compressed generally tubular substrate defining a longitudinal axis, a plurality of expandable segments disposed over the substrate and spaced apart along the longitudinal axis, and a graft member positioned over the segments, the graft member including a network of cells and hinges, each cell configured to cover at least a portion of an expandable segment, adjacent cells connected to one another by at least one hinge.

In another embodiment, an implantable prosthesis includes a longitudinally compressed generally tubular substrate defining a longitudinal axis, a plurality of expandable segments disposed over the substrate and spaced apart along the longitudinal axis, and a plurality of filaments, adjacent expandable segments connected by a first filament and a second filament spaced approximately 180 degrees from the first filament.

In one embodiment, a method of forming an implantable prosthesis includes compressing a generally tubular substrate defining a longitudinal axis from a first length to a second length shorter than the first length, disposing a plurality of expandable segments over the substrate, spaced apart along the longitudinal axis, and positioning a graft member with a lattice structure over the segments to cover at least a portion of each expandable segment.

In another embodiment, a method of forming an implantable prosthesis includes compressing a generally tubular ePTFE member from a first length to a second length shorter than the first length, disposing a plurality of expandable segments over the substrate, spaced apart along a longitudinal axis thereof, and tensioning a graft member with a lattice structure over the segments to cover at least a portion of each expandable segment.

In yet another embodiment, a method of forming an implantable prosthesis includes compressing a generally tubular substrate defining a longitudinal axis from a first length to a second length shorter than the first length, disposing a plurality of expandable segments over the substrate, spaced apart along the longitudinal axis, and connecting adjacent expandable segments with a first filament and a second filament spaced approximately 180 degrees from the first filament.

These and other embodiments, features and advantages will become more apparent to those skilled in the art when taken with reference to the following more detailed description of the invention in conjunction with the accompanying drawings that are first briefly described.

BRIEF DESCRIPTION OF THE DRAWINGS

FIG. 2D is a perspective view of a section of the stent-graft of FIG. 2C, shown in a bent configuration.

FIG. 3 is a perspective view of one embodiment of an annular stent member.

FIG. 4A is a partial perspective view of one embodiment of a stent-graft.

FIG. 4B is an enlarged view of one stent strut configuration of the stent-graft in FIG. 4A.

DESCRIPTION OF THE PREFERRED EMBODIMENTS

Figure 1A:
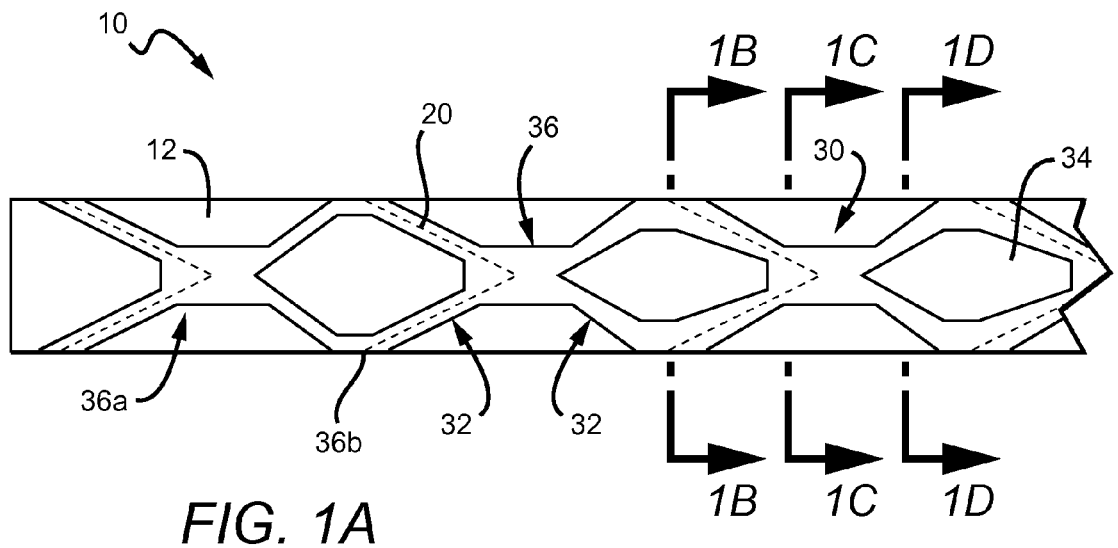
FIG. 1A is a perspective view of one embodiment of a stent-graft.

The following description should be read with reference to the drawings, in which like elements in different drawings are identically numbered. The drawings, which are not necessarily to scale, depict selected embodiments and are not intended to limit the scope of the invention. The description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment.

The stent-graft described herein may be utilized with bio-active agents. Bio-active agents can be coated onto a portion or the entirety of the stent and/or graft for controlled release of the agents once the stent-graft is implanted. The bio-active agents can include, but are not limited to, vasodilator, anti-coagulants, such as, for example, warfarin and heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

As used herein, the term "bio-resorbable" includes a suitable bio-compatible material, mixture of materials or partial components of materials being degraded into other generally non-toxic materials by an agent present in biological tissue (i.e., being bio-degradable via a suitable mechanism, such as, for example, hydrolysis) or being removed by cellular activity (i.e., bioresorption, bioabsorption, or bioresorbable), by bulk or surface degradation (i.e., bioerosion such as, for example, by utilizing a water insoluble polymer that is soluble in water upon contact with biological tissue or fluid), or a combination of one or more of the bio-degradable, bio-erodable, or bio-resorbable material noted above. Potential materials for the stent described herein include, for example, biodegradable polymers such as polylactic acid, i.e., PLA, polyglycolic acid, i.e., PGA, polydioxanone, i.e., PDS, polyhydroxybutyrate, i.e., PHB, polyhydroxyvalerate, i.e., PHV and copolymers or a combination of PHB and PHV (available commercially as Biopol®), polycaprolactone (available as Capronor®), polyanhydrides (aliphatic polyanhydrides in the back bone or side chains or aromatic polyanhydrides with benzene in the side chain), polyorthoesters, polyaminoacids (e.g., poly-L-lysine, polyglutamic acid), pseudo-polyaminoacids (e.g., with back bone of polyaminoacids altered), polycyanocrylates, or polyphosphazenes.

The stent may be formed of a shape memory material, including, for example, shape memory metals, shape memory alloys, super elastic shape memory metal alloys, linear elastic shape memory alloy, shape memory polymers, and combinations thereof. One preferred shape memory material is Nitinol. The stent may also be formed of metals, such as, for example, stainless steel, platinum, and Elgiloy, or certain polymers.

Potential materials for a substrate and/or graft member include, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene fibers, aramid fibers, and combinations thereof. One preferred embodiment for a substrate material is ePTFE, while a preferred embodiment for a graft member material is high strength polymer fibers such as ultra high molecular weight polyethylene fibers (e.g., Spectra®, Dyneema Purity®, etc.) or aramid fibers (e.g., Technora®, etc.). The substrate and/or graft member may include a bioactive agent. In one preferred embodiment, an ePTFE substrate includes a carbon component along a blood contacting surface thereof.

The examples discussed herein may include an ePTFE substrate. As is known in the art, an ePTFE substrate may be manufactured in a number of ways, including, for example, extrusion of a tube (seamless), extrusion of a sheet that is subsequently formed into a tube (one or more seams), helical wrapping of ePTFE tape around a mandrel (e.g., multiple seams or preferably a single helical seam), etc. While the preferred method used for forming an ePTFE substrate in the present invention is to extrude a tube, it should be appreciated that other forming methods are possible and are within the scope of the invention. The substrate and/or graft member of the stent-graft described herein has a thickness in the range of approximately 10 microns to approximately 100 microns, preferably in the range of approximately 20 microns to approximately 60 microns. The node-fibril microstructure of an ePTFE substrate may include various orientations for the fibrils, but in a preferred embodiment, the fibrils are oriented generally parallel to the longitudinal axis of the substrate. The average internodal distance (IND) for one preferred embodiment of a substrate and/or graft described herein is in the range of approximately 6 microns to approximately 80 microns. Also, as described in U.S. Pat. No. 5,790,880 to Banas et al., which is incorporated by reference in its entirety in this application, the substrate and/or graft member may be made of an ePTFE that undergoes nodal elongation during radial expansion.

The ePTFE substrate in the described examples herein is preferably longitudinally compressed prior to attachment of a stent member and, in some embodiments, a graft member. Longitudinal compression of an ePTFE graft is described in U.S. Pat. No. 4,955,899 to Della Coma et al. and is incorporated by reference in its entirety in this application. Applicant has discovered that a large increase in stent-graft flexibility can be achieved with a small reduction in the length of the substrate. Further, Applicant has discovered that longitudinal compression of the substrate in combination with stent-graft elements and methods of making a stent-graft described herein results in a stent-graft that has enhanced stretching capability, permitting positioning of the stent-graft through and/or into curved/tortuous sections of a blood vessel or graft without kinking.

Markers M1, M2, M3, M4 . . . Mn can be provided for all of the embodiments described herein. The marker Mn can be formed from the same material as the stent as long as the material is radiographic or radiopaque. The marker material can also be formed, for example, from gold, tantalum, platinum, and combinations thereof. One or more markers can be formed from a marker material different from other markers.

Referring now to FIG. 1A, a stent-graft 10 including a substrate 12, a stent member 20 and a graft member 30 is shown. The stent member may be cut from a tube of shape memory material (e.g., Nitinol) and may include, for example, a plurality of expandable segments in the form of discrete annular members spaced along a surface of the substrate, windings of an elongate continuous member helically disposed with respect to the substrate, interconnected members disposed over the substrate, combinations thereof, etc. The graft member 30 has a generally tubular shape and is configured in a honeycomb-type pattern or lattice structure, including a plurality of cells 32 with each cell 32 having a central opening 34. While the central opening 34 has a heptagon shape in the embodiment shown, other geometric shapes, including polygonal shapes, are possible and within the scope of the invention. The cells 32 are connected together via hinges 36, each hinge including a point of pivot to permit rotational pivoting motion thereof. In a preferred embodiment, the hinges 36 are arranged in spaced apart sets of two, the first hinge in a given set positioned circumferentially approximately 180 degrees apart from the second hinge, and adjacent sets of hinges are rotated approximately 90 degrees from one another. Thus, for example, referring to FIG. 1A, longitudinal hinges 36a connect adjacent cells 32 in a first row of cells and adjacent cells 32 in a second row of cells located opposite the first row of cells (spaced circumferentially approximately 180 degrees therefrom), while circumferential hinges 36b, rotated approximately 90 degrees with respect to longitudinal hinges 36a, connect each cell in the first row of cells with its circumferential counterpart in the second row of cells in two locations spaced approximately 180 degrees apart (i.e., first row cells are connected to second row cells at approximately the same axial position along the longitudinal axis by two circumferential hinges).

Figure 1B:
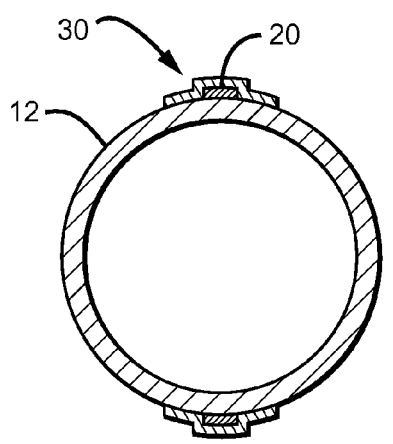
FIG. 1B is a cross-sectional view of the stent-graft of FIG. 1A, taken along line B-B.
Figure 1C:
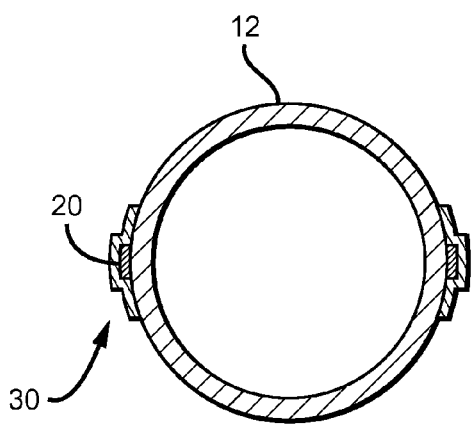
FIG. 1C is a cross-sectional view of the stent-graft of FIG. 1A, taken along line C-C.
Figure 1D:
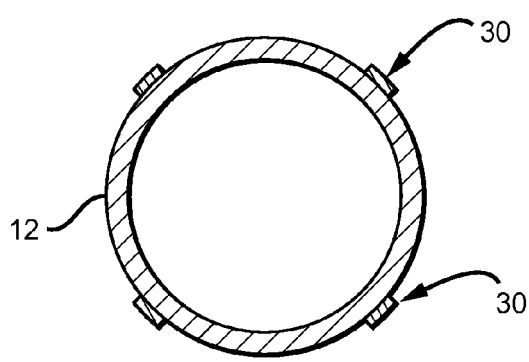
FIG. 1D is a cross-sectional view of the stent-graft of FIG. 1A, taken along line D-D.

FIGS. 1B-1D show cross-sectional views of the stent-graft 10 at different positions along a longitudinal axis thereof. FIG. 1B is a cross-section taken through a middle section of a cell 32, essentially bisecting circumferential hinges 36b. In this view, a cross-section of a stent member 20 is seen covered by graft member 30 at two locations separated circumferentially approximately 180 degrees. FIG. 1C is a cross-section taken through a longitudinal hinge 36a, again showing a cross-section of a stent member 20 covered by graft member 30 at two locations separated circumferentially approximately 180 degrees. The two sections of stent member 20 in this view, however, are offset approximately 90 degrees from the sections of stent member 20 shown in FIG. 1B. FIG. 1D is a cross-section taken through a cell 32 of graft member 30, showing the position of the graft member 30 in direct contact with the substrate 12.

Figure 2A:
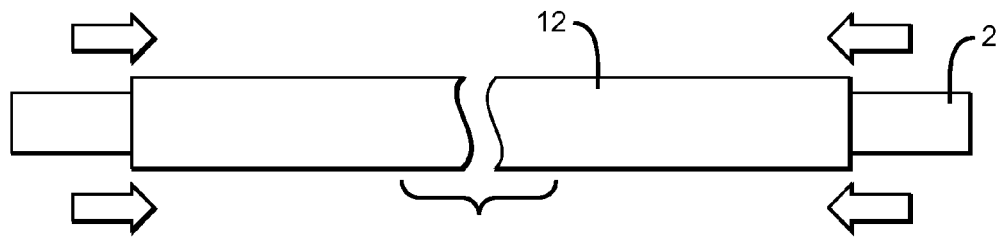
FIG. 2A is a depiction of one step in the making of a preferred embodiment of a stent-graft.
Figure 2B:
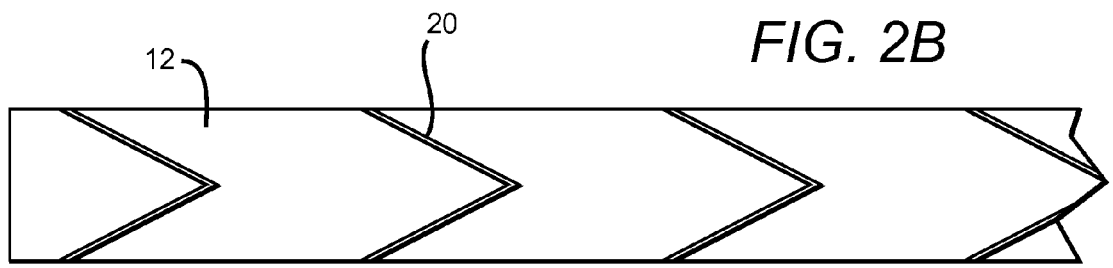
FIG. 2B is a depiction of another step in the making of the stent-graft.
Figure 2C:
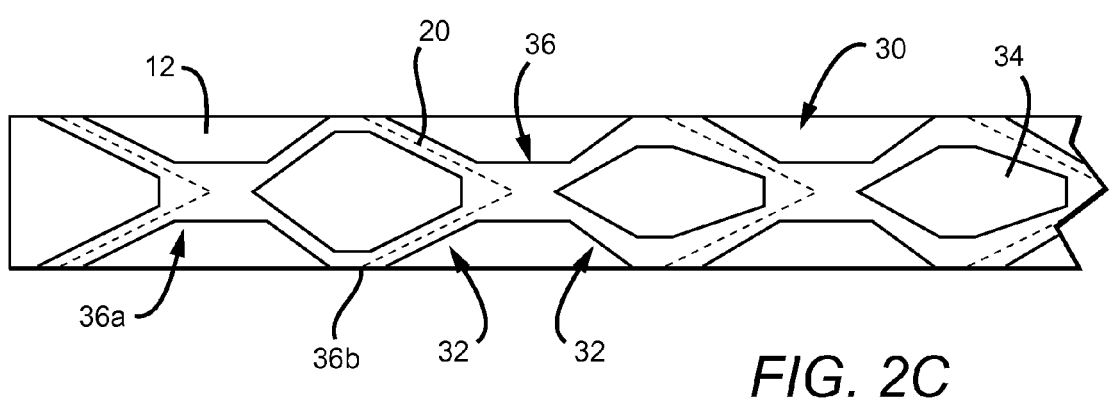
FIG. 2C is a depiction of another step in the making of the stent-graft.

In one preferred embodiment, the stent-graft 10 includes an ePTFE substrate 12, a shape memory stent member 20 and a graft member 30 knitted or woven from ultra high molecular weight polyethylene fibers. The stent member 20 includes a plurality of discrete annular members spaced apart along a longitudinal axis of the substrate 12. In a preferred method of assembly, the substrate 12 is positioned over a mandrel 2 and longitudinally compressed in a range of approximately 50% to approximately 97% of its original, uncompressed length, as depicted in FIG. 2A. While the substrate 12 is held in its compressed state, the annular members are positioned over an outer surface of the substrate 12 and spaced a predetermined distance from one another. The annular members may optionally include a coating of polycarbonate urethane. Once the annular members are in the predetermined position over the substrate 12, the graft member 30 is positioned over the annular members and longitudinally compressed substrate 12. The graft member 30 is then placed under tension (e.g., proximal and distal ends of the graft member are pulled in opposite directions) and clamped or otherwise fixed in place over the annular members and compressed substrate 12. In this tensioned state, the material of the graft member 30 may cover substantially all of, or only a portion of, an outer surface of the annular members. The stent-graft 10 in its assembled form is then preferably contacted with a polymeric adhesive, such as polyurethane, to bond the graft member 30 to the annular members and/or the substrate 12. Optionally, the polymeric adhesive can be activated by a solvent, such as tetrahydrofuran (THF). Other modes of attachment (e.g., resin, sutures, heat, pressure, etc.) may also be used in conjunction with the solvent to assist in bonding.

In FIG. 2D, a portion of the stent-graft 10 made according to the aforementioned preferred method is shown in a curved state. Due to the longitudinal compression of the substrate 12 and flexibility of the graft member 30, the portion of the stent-graft 10 following the longer path of curvature C1 stretches, while the portion of the stent-graft 10 following the shorter path of curvature Cs compresses, such that structural integrity of the stent-graft 10 is maintained. The longitudinal hinges 36a and circumferential hinges 36b together produce a multiple hinge effect in graft member 30, which imparts enhanced flexibility to the graft member 30. The bending freedom of the substrate 12 together with the flexibility of the graft member 30 (due at least in part to the rotational freedom of the hinges 36) is believed to impart superior kink resistance to the stent-graft 10 such that the stent-graft 10 is able to navigate tortuous bends without kinking. Other advantages of stent-graft 10 are believed to include, for example, excellent axial compressibility, the potential of increased radial strength due to the design of the stent-graft (i.e., the radial strength decreases as the stent length increases and the stent-graft can only extend to the tensioned length of the graft member 30, thus limiting this decrease in radial strength), accurate positioning due to the tensioning of the graft member 30 (i.e., the stent-graft can only extend to the tensioned length of the graft member 30), and durability imparted by the fatigue-resistant hinges of the graft member 30.

In certain embodiments, the annular members include a balloon expandable material and are arranged over the substrate 12 in an original or non-expanded configuration with a original perimeter. In one embodiment of treating a blood vessel, a stent-graft including balloon expandable annular members is positioned over a length of a balloon on a balloon catheter, which may be a component of a delivery system (e.g. the balloon catheter may be coaxially disposed in an outer sheath). The balloon catheter/delivery system is inserted intraluminally in a patient to a predetermined region of a blood vessel and the balloon is then inflated to expand the stent-graft, the annular members expanding to an expanded configuration with an expanded perimeter larger than the original perimeter. After positioning is confirmed, the balloon is deflated and the balloon catheter removed from the blood vessel. In other embodiments, the annular members include a self-expanding material and are arranged over the substrate 12 in an expanded configuration defining an expanded perimeter. In one embodiment of treating a blood vessel, a stent-graft including self-expanding annular members is first compressed, the annular members collapsing to a collapsed configuration with a collapsed perimeter smaller than the expanded perimeter. A constraining sheath, which may be a component of a delivery system, is positioned over the stent-graft to maintain the annular members in the collapsed configuration and the sheath is delivered intraluminally in a patient to a predetermined region of a blood vessel. The constraining sheath is then removed from the stent-graft, allowing the annular members to expand. A balloon can optionally be inserted and inflated thereafter to ensure contact of the stent-graft with the blood vessel wall and positioning of the stent-graft in the blood vessel. The annular members, whether balloon-expandable, self-expandable, or a combination thereof, may include a bio-resorbable material.

In one embodiment shown in FIG. 3, the stent member 20 comprises annular members including struts 22 arranged in an undulating configuration that is preferably closed ended. The struts 22 intersect at an apex to form a first set of apices 24 and a second set of apices 26 offset therefrom, such that annular members of stent member 20 include an equal number of first and second apices 24, 26. Each apex includes a peak P and a trough T. The lengths of the struts 22 may be uniform, as shown, or may be varied about the circumference of the annular member. For example, the annular member could include two or more strut lengths arranged in patterns about its circumference. Many other annular member configurations are also possible and are within the scope of the invention, such as, for example, sinusoidal patterns, meandering curve patterns, other curvilinear patterns, etc. The struts may be substantially straight along their lengths, as shown, or may be curved or wave-like. Any type of pattern and/or strut length or shape can be combined with other patterns and/or strut lengths or shapes to form a non-uniform annular member. Moreover, it should be appreciated that the shape, size, thickness, material and/or other characteristic of the annular members can be varied along the length of the stent-graft. Further, the undulations are not limited to zig-zag patterns but can be wave-like in pattern. The wave-like pattern can also be generally sinusoidal in that the pattern may have the general form of a sine wave, whether or not such wave can be defined by a mathematical function. Alternatively, any wave-like forms can be employed so long as it has amplitude and displacement. For example, a square wave, saw tooth wave, or any applicable wave-like pattern defined by the struts where the struts have substantially equal lengths or unequal lengths.

In one embodiment, annular members of stent member 20 are positioned along a surface of a longitudinally compressed substrate 12 so that the peak P of a first annular member of stent member 20 is aligned with a trough T of an adjacent annular member of stent member 20, the adjacent annular members of stent member 20 being spaced a sufficient distance apart to prevent interference between the annular members of stent member 20 upon radial compression of the stent-graft. For example, the annular members of stent member 20 (including a self-expanding material) may be attached to a substrate in an expanded configuration defining an expanded perimeter of the annular members of stent member 20 and are subsequently radially compressed for delivery to a blood vessel to a collapsed configuration, defining a collapsed perimeter of the annular members of stent member 20 smaller than the expanded perimeter of the annular members of stent member 20. The sufficient distance between adjacent annular members to prevent interference is dependent on a variety of factors, such as, for example, length, shape, and/or other characteristics of the struts, but in a preferred embodiment with annular members of stent member 20 having a uniform strut length of approximately 500 microns to approximately 1500 microns and having peaks P and troughs T of adjacent annular members of stent member 20 aligned, a sufficient distance between adjacent annular members of stent member 20 is in the range of approximately 0.1 millimeter to approximately 1 millimeter. In other embodiments, adjacent annular members of stent member 20 may have peaks P and/or troughs T offset circumferentially to each other.

In certain embodiments, the stent member includes one or more elongate members helically disposed about an outer surface of a longitudinally compressed substrate 12. In the embodiment shown in FIG. 4A, an elongate member 40 is helically wound about an outer surface of the substrate 12 such that adjacent helical windings are spaced a distance d from one another. In one embodiment, the distance d between adjacent helical windings of elongate member 40 is approximately equal along the length of the stent-graft. In other embodiments, the distance between adjacent helical windings may be varied along the length of the stent-graft. For example, beginning at one end of the stent-graft 10, the distance between the first two helical windings, d1, could be less than the distance d2 between subsequent helical windings. The distance between adjacent helical windings could then progressively become greater along the length of the stent-graft, could alternate between d1 and d2, etc. In embodiments including two or more elongate members, the members could be helically wound about the substrate in different directions and/or with different helical angles. In certain embodiments, the elongate member 40 is placed under tension as it is helically wound about the substrate.

In one embodiment, the elongate member 40 includes struts arranged with respect to each other and the longitudinal axis L of the stent-graft 10 as shown in FIGS. 4A-4B. Such an arrangement is believed to impart to the stent-graft an ability to deploy without substantially shortening. Elongate member 40 includes a plurality of zig-zag struts, including a longer first strut 42 and a shorter second strut 44 that alternate along the length of the elongate member 40. The first strut 42 and second strut 44 intersect at an apex 46 to form a first angle Φ between the first and second struts 42, 44. The bisection of first angle Φ by a line parallel to the longitudinal axis L of the stent-graft results in two substantially equivalent second and third angles θ as shown in FIG. 4B. Each apex 46 forms a peak P and a trough T and the elongate member 40 includes a first set of apices 48 spaced from a second set of apices 49 along its length.

In one embodiment, helical windings of an elongate member are positioned along a surface of a longitudinally compressed substrate so that the peak P of apices 48 on one helical winding is aligned with a trough T of apices 48 on an adjacent helical winding, the adjacent windings spaced a sufficient distance apart to prevent interference between the windings upon radial compression of the stent-graft. For example, the elongate member 40 may be coupled to a substrate in an expanded configuration defining an expanded perimeter of the stent-graft and subsequently radially compressed for delivery to a blood vessel to a collapsed configuration, defining a collapsed perimeter of the stent-graft smaller than the expanded perimeter thereof. In another embodiment, the distance between adjacent helical windings is such that regardless of alignment, radial compression of the stent-graft will not result in interlocking of the struts.

Figure 5A:
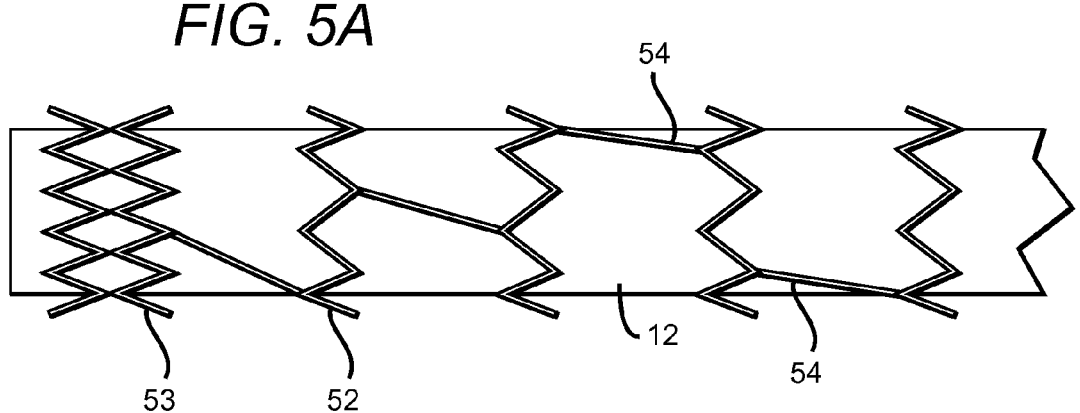
FIG. 5A is a perspective view of one embodiment of a stent-graft with filaments connecting expandable segments.
Figure 5B:
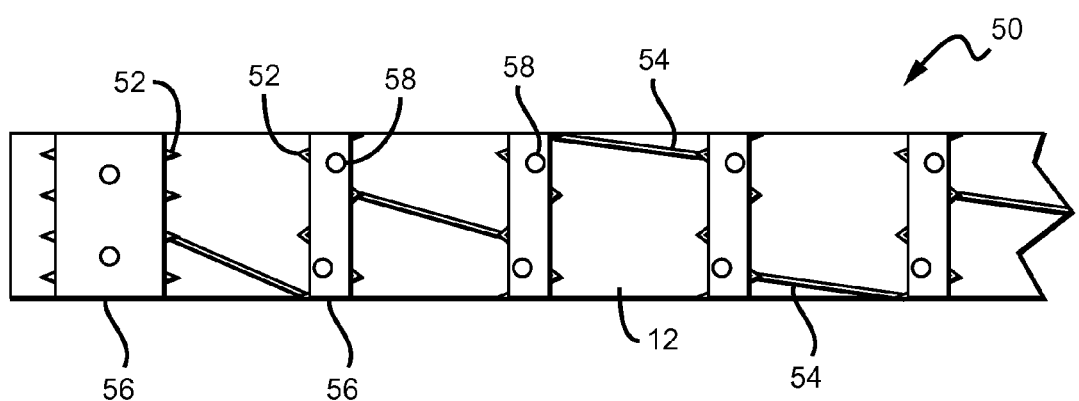
FIG. 5B is a perspective view of the stent-graft in FIG. 5A with circumferential bands covering at least a portion of the expandable segments.

FIGS. 5A-5B illustrate another embodiment of a stent-graft 50. In this embodiment, a stent member includes a plurality of expandable segments, such as discrete annular members 52 (e.g., including zig-zag struts) positioned over an outer surface of a substrate 12. In other embodiments, the stent member may be an elongate member helically disposed about the outer surface of the substrate or other stent member forms described herein. In a preferred embodiment the substrate is a longitudinally compressed ePTFE tube. FIG. 5A shows the annular members 52 spaced apart along a longitudinal axis of the substrate 12 with adjacent annular member 52 connected by filaments 54. The filaments 54 may include a material such as, for example, polyester, polytetrafluoroethylene, tensioned polytetrafluoroethylene, tensioned expanded polytetrafluoroethylene, silicones, urethanes, ultra high molecular weight polyethylene, polyamides, polyimides, polyaramides, isophthalamides, terephthalamides, fluorocarbons, and combinations thereof. In a preferred embodiment, the filaments are made of a high strength material, such as ultra high molecular weight polyethylene, which is distinct from the material of the stent member (e.g., annular members).

The filaments 54 have a first end connected to a first annular member 52 and a second end connected to a second annular member adjacent the first annular member. For embodiments in which the annular members 52 include connected struts in a zig-zag configuration forming apices, the filaments may connect the annular members in peak-to-peak fashion, as shown in FIG. 5A. The annular members may be arranged so that the connected peaks of adjacent annular members are offset, the filament lying at an angle with respect to the longitudinal axis of the substrate 12, or may be arranged so that the connected peaks of adjacent members are generally aligned, the filament lying substantially parallel to the longitudinal axis of the substrate 12. Other embodiments can include peak-to-trough connections of the filament. As shown in FIG. 5A, selected adjacent annular members may be connected together at opposing peaks to form an enlarged annular member 53 with a diamond shape pattern. Such enlarged annular members may be positioned at the ends of the substrate and/or along the length of the substrate. Attachment of the filaments to the stent member (e.g., annular members) may be accomplished by methods known to one skilled in the art, including, for example, the use of polymeric adhesives, heat bonding, sewing, ultrasonic bonding, solvent bonding, encapsulation, and combinations thereof.

In a preferred embodiment, a first and second filament connects each pair of adjacent annular members, the second filament spaced circumferentially approximately 180 degrees from the first filament in a dual hinge arrangement believed to increase flexibility of the stent-graft while providing a stable structure. The first and second filaments between a first pair of adjacent annular members may be offset from first and second filaments between a second pair of adjacent annular members, as shown in FIG. 5A. The filaments may be arranged in a pattern along the length of the substrate, such as, for example, a pattern in which filaments between adjacent pairs of annular members are offset a predetermined number of peaks from the connection points on the common annular member.

FIG. 5B illustrates an optional outer layer for the stent-graft 50 of FIG. 5A to attach the annular members 52, 53 to the longitudinally compressed substrate in addition to, or instead of, other attachment methods, such as, for example, selective application of adhesives, applying a polymer to the annular members 52, 53 and bonding with a solvent, use of sutures to stitch the annular members to the substrate, etc. The circumferential bands 56 are positioned over the annular members 52 and 53 and bonded to the substrate 12 by heating, which in a preferred embodiment is accomplished through selective bonding at discrete bonding locations 58. The circumferential bands 56 may include a material such as, for example, polytetrafluoroethylene, expanded polytetrafluoroethylene, fine metal meshes, linear polyethylene, polymers, and combinations thereof. The circumferential bands 56 may differ with respect to one or more characteristics or properties and/or may be made of different materials along the length of the stent-graft 50. For example, thicknesses or widths of the bands 56 may differ along the length of the stent-graft 50 to impart desired functionality, porosity or fibril orientation may differ from band to band, the shapes of the bands 56 may differ according to placement along the length of the stent-graft 50 (e.g., wider bands are utilized for enlarged annular members 53), etc.

In one embodiment, the circumferential bands 56 are continuous, closed rings of material, while in other embodiments, the bands are longitudinal strips of material with a first and second end that are circumferentially wrapped over the stent member such that the first and second ends overlap. In still other embodiments, longitudinal strips of material are used in combination with, or instead of, the circumferential bands and are positioned over one or more bands and/or filaments. The longitudinal strips may be arranged over the substrate generally parallel to the longitudinal axis thereof or at an angle therewith. One or more strips may also be helically wound about the substrate and stent member with a constant pitch or one that varies along the length of the stent-graft.

In a preferred embodiment, the substrate is an ePTFE tube that is longitudinally compressed in the range of approximately 50% to approximately 97% of its starting uncompressed length. More preferably, the ePTFE tube is longitudinally compressed in the range of approximately 80% to approximately 95% of its starting uncompressed length. The stent member/filament arrangement is then spaced apart along the length of the substrate that is maintained in the compressed state (in other embodiments, the filaments may be attached to the stent member following positioning over the substrate). Circumferential ePTFE bands are then disposed over the stent member, substantially covering the stent member, but leaving the filaments substantially uncovered. The circumferential bands are then heated at discrete bonding locations to selectively sinter the ePTFE bands to the ePTFE substrate, capturing the stent member therebetween. The bonding locations 58 for each circumferential band 56 may be selected in a particular pattern to enhance structural stability of the stent-graft and reduce the possibility of delamination. In a preferred embodiment, four (4) bonding locations are selected for each circumferential band.

This invention has described and specific examples have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A method of forming an implantable prosthesis, comprising:
   compressing a generally tubular substrate defining a longitudinal axis from a first length to a second length shorter than the first length;
   disposing a plurality of expandable segments over the substrate, spaced apart along the longitudinal axis; and
   tensioning a graft member with a lattice structure over the segments to cover at least a portion of each expandable segment and fixing the graft member in place over the segments and the tubular substrate while the graft member is in the tensioned state and the tubular substrate is in the compressed state.

2. The method according to claim 1, further comprising coating the graft member with a polymeric adhesive and bonding the graft member to at least one of the expandable segments and the substrate.

3. The method according to claim 2, further comprising contacting the graft member with a solvent to activate the polymeric adhesive.

4. The method according to claim 3, wherein the solvent comprises tetrahydrofuran (THF).

5. The method according to claim 1, further comprising coating the expandable segments with a polymeric adhesive and bonding the expandable segments to the substrate and the graft member.

6. The method according to claim 1, wherein the lattice structure comprises cells connected by hinges, the cells including a central opening defining a geometric shape, the positioning step including spacing the central opening of each of the cells from at least a portion of one or more expandable segments.

7. The method according to claim 1, wherein the compressing step comprises compressing the substrate to the second length in the range of approximately 50% to approximately 97% of the first length.

8. A method of forming an implantable prosthesis, comprising:
   compressing a generally tubular ePTFE member from a first length to a second length shorter than the first length;
   disposing a plurality of expandable segments over the ePTFE member, spaced apart along a longitudinal axis thereof; and
   tensioning a graft member with a lattice structure over the segments to cover at least a portion of each expandable segment and fixing the graft member in place over the segments and the tubular substrate while the graft member is in the tensioned state and the tubular substrate is in the compressed state.

9. The method according to claim 6, wherein the central opening of the cells defines a heptagon shape, the positioning including spacing the heptagon shape of the central opening of each of the cells from at least a portion of one or more expandable segments.

10. The method according to claim 7, wherein the compressing comprises compressing the substrate to the second length in the range of approximately 80% to approximately 95% of the first length.

11. The method according to claim 1, wherein tensioning the graft member includes pulling proximal and distal ends of the graft member in opposite directions.

12. The method according to claim 1, wherein the disposing includes spacing the plurality of expandable segments apart a sufficient distance along the longitudinal axis to prevent interference between the expandable segments upon radial compression of the implantable prosthesis.

13. The method according to claim 1, wherein the disposing includes helically disposing at least one of the plurality of expandable segments over the substrate.

14. The method according to claim 8, wherein the tensioning includes pulling proximal and distal ends of the graft member in opposite directions.

15. The method according to claim 8, wherein the ePTFE member includes a carbon component along an abluminal surface thereof, the disposing and the tensioning comprising leaving at least a portion of the carbon component uncovered.

16. The method according to claim 8, wherein the ePTFE member includes a microstructure of nodes and fibrils, the fibrils being oriented generally parallel to the longitudinal axis of the ePTFE member, the compressing causing nodes of the microstructure to move axially closer together.

17. The method according to claim 8, wherein the lattice structure comprises cells connected by hinges, the cells including a central opening defining a geometric shape, the positioning including spacing the central opening of each of the cells from at least a portion of one or more expandable segments.

* * * * *